US008765211B2

(12) United States Patent
O'Neill et al.

(10) Patent No.: US 8,765,211 B2
(45) Date of Patent: Jul. 1, 2014

(54) METHOD FOR COATING METAL IMPLANTS WITH THERAPEUTIC MIXTURES

(75) Inventors: Liam O'Neill, Midleton (IE); Caroline O'Sullivan, Clonakity (IE)

(73) Assignee: Enbio Limited, Dublin (IE)

( * ) Notice: Subject to any disclaimer, the term of this patent is extended or adjusted under 35 U.S.C. 154(b) by 287 days.

(21) Appl. No.: 13/254,569

(22) PCT Filed: Mar. 31, 2010

(86) PCT No.: PCT/IB2010/000927

§ 371 (c)(1), (2), (4) Date: Feb. 9, 2012

(87) PCT Pub. No.: WO2010/113033

PCT Pub. Date: Oct. 7, 2010

(65) Prior Publication Data

US 2012/0135133 A1 May 31, 2012

Related U.S. Application Data

(60) Provisional application No. 61/164,952, filed on Mar. 31, 2009.

(51) Int. Cl.
*A61L 33/00* (2006.01)

(52) U.S. Cl.
USPC .......................................... 427/2.27; 424/423

(58) Field of Classification Search
USPC .......................................... 424/423; 427/2.25
See application file for complete search history.

(56) References Cited

U.S. PATENT DOCUMENTS

2006/0193890 A1* 8/2006 Owens et al. ................. 424/423
2009/0061071 A1 3/2009 McMorrow

FOREIGN PATENT DOCUMENTS

WO WO 01/17577 A1 3/2001
WO WO 2008/033867 A2 3/2008
WO WO 2008/151299 A2 12/2008

OTHER PUBLICATIONS

International Search Report of PCT/IB/2010/000927 dated Dec. 3, 2010.

Popat et al., "Decreased staphylococcus epidermis adhesion and increased osteoblast functionality on antibiotic-loaded titania nanotubes", Biomaterials, vol. 28, No. 32, Aug. 24, 2007, pp. 4880-4888.

Alt, et al., "The effects of combined gentamicin-hydroxyapatite coating for cementless joint prosthesis on the reduction of infection rates in a rabbit infection prophylaxis model", Biomaterials, vol. 27, No. 26, Sep. 1, 2006, pp. 4627-4634.

Schnettler et al., "Glycerol-I-lactide coating polymer leads to delay in bone ingrowth in hydroxyapatite implants", J. Controlled Release, vol. 106, 2005, pp. 154-161.

(Continued)

*Primary Examiner* — Dah-Wei D Yuan
*Assistant Examiner* — Andrew Bowman
(74) *Attorney, Agent, or Firm* — Bookoff McAndrews, PLLC

(57) ABSTRACT

Disclosed herein are methods of treating an article surface. The method comprises delivering a polymer and drug to a medical implant having a porous surface and using at least one particle stream from at least one fluid jet to subsequently remove the polymer from the outer surface of the metal substrate, thereby retaining the therapeutic agent and polymer within the pores of the implant.

18 Claims, 2 Drawing Sheets

(56) References Cited

OTHER PUBLICATIONS

Solomon et al., "The high-temperature wetting balance and the influence of grit blasting on brazing of IN718", Welding Research, 2003, pp. 278-287.

Momber et al., "Hydrodynamic profiling and grit blasting of low-carbon steel surfaces", Tribology International, vol. 35, 2002, pp. 271-281.

Arola et al., "Abrasive waterjet peening: a new method of surface preparation for metal orthopedic implants", J. Biomed, Mat. Res., 2000, 53(5), pp. 536-546.

Arola et al., "Parametric effects on particle deposition in abrasive waterjet surface treatments", Machining Science and Technology, 2004, 8(2), pp. 171-192, Abstract.

Ishikawa et al., "Blast coating method: new method of coating titanium surface with hydroxyapatite at room temperature", J. Biomed. Mat. Res. 1997, pp. 129-134.

Cook et al., "Optimum pore size for bone cement fixation", Clinical Orthopaedics and Related Research, Oct. 1997, 223, Abstract.

Chang et al., "Excimer pulsed laser ablation of polymers in air and liquids for micromachining applications", J. Manufacturing Processes, 1999, 1(1), pp. 1-17.

Urech et al., "Polymer ablation: from fundamentals of polymer design to laser plasma thruster", Applied Surface Science, 2007, 253, pp. 6409-6415.

Lu et al., "Micro and nano-fabrication of biodegradable polymers for drug delivery", Advanced Drug Delivery Reviews, 2004, 56, 1621-1633.

Liow, "Mechanical micromachining: a sustainable micro-device manufacturing approach?", Journal of Cleaner Production, 2009, 17, pp. 662-667.

Rajta et al., "Proton beam micromachining on PMMA, Foturan and CR-39 materials", Nuclear Instruments and methods in Physics Research B 210, 2003, pp. 260-265.

Springham et al., "Micromachining using deep ion beam lithography", Nuclear Instruments and Methods in Physics Research, B 130, 1997, 1-4, pp. 155-159.

Martin et al., "Electron beam lithography at 10 keV using an epoxy based high resolution negative resist", Microelectronic Engineering, 2007, 84, pp. 1096-1099.

* cited by examiner

METHOD FOR COATING METAL IMPLANTS WITH THERAPEUTIC MIXTURES

RELATED APPLICATION

This application is a national phase application of PCT/IB2010/000927, filed Mar. 31, 2010, which claims the benefit of priority under 35 U.S.C. §119(e) to U.S. Prov. App. 61/164,952, filed Mar. 31, 2009, the disclosures of which are incorporated herein in their entirety by reference.

FIELD OF THE INVENTION

The present invention relates to methods of treating the surfaces of medical implants with therapeutically effective agents.

BACKGROUND OF THE INVENTION

Metallic implants are widely utilized in modern medicine. Metals such as titanium, cobalt chrome, nitinol and stainless steel are widely used as implant materials due to their combination of strength, corrosion resistance and biocompatibility. These metals are commonly found in orthopaedic implants, where they are offered as either cemented or cementless implants, depending on whether a cement is used to hold the implant in place. These implants are routinely roughened to produce a surface onto which osteoblasts can attach and proliferate to promote bone fixation. Early implants achieved this roughening through simple processes such as grit blasting. More modern designs are focused around complex surface geometries based on three dimensional surfaces. For instance, DePuy provides a surface termed Porocoat®, which is derived from sintered metal beads. A further enhancement on this surface is their Gription® surface. Stryker also provides a beaded metal surface and is developing a laser process termed SLM (selective laser melting) to deliver a three dimensional surface. Zimmer have launched a porous metal finish called Trabecular Metal™. Other versions such as plasma sprayed Ti foam are well known in the medical device industry. Although these surfaces are different, they all share a common concept in that they are open, porous three dimensional metal surfaces designed to optimize bone growth and implant fixation.

There remain, however, on-going issues relating to microbial infections with these implants. Infections can be pre-existing, introduced during surgery or can migrate to the implant surface post operatively. Infection can induce bone degeneration that can loosen the implant. As a consequence, expensive, complex and difficult revision surgery with prolonged and extensive antimicrobial agent administration may be necessary.

Numerous attempts have been made to minimize infections through strategies such as adding antibiotics to bone cements. This provides an elution of drugs from the cement, which helps to eliminate microbes in the vicinity of the implant during early stage fixation. Other attempts have focused on trying to attach active agents such as antibiotics to the surface of the metal implant. Simply dipping the metal implant in antibiotic solution can result in a drug elution profile having a burst release of very short duration. Thus, this approach offers limited value. Slow elution has been attempted by entrapping the drugs in a polymer coating on the implant surface and these drug loaded polymeric coatings are well established in medical devices. For example, the drug eluting stents now dominate the stent market and are designed to deliver therapeutic agents over several weeks or months.

However, this solution is not applicable to the hard tissue sector, as the presence of the polymer coating on the biocompatible metal implant surface can impede bone fixation. Therefore an alternative strategy is called for.

BRIEF DESCRIPTION OF THE DRAWINGS

Various embodiments of the invention will be understood from the following description, the appended claims and the accompanying drawings, in which:

DETAILED DESCRIPTION

Figure 1:
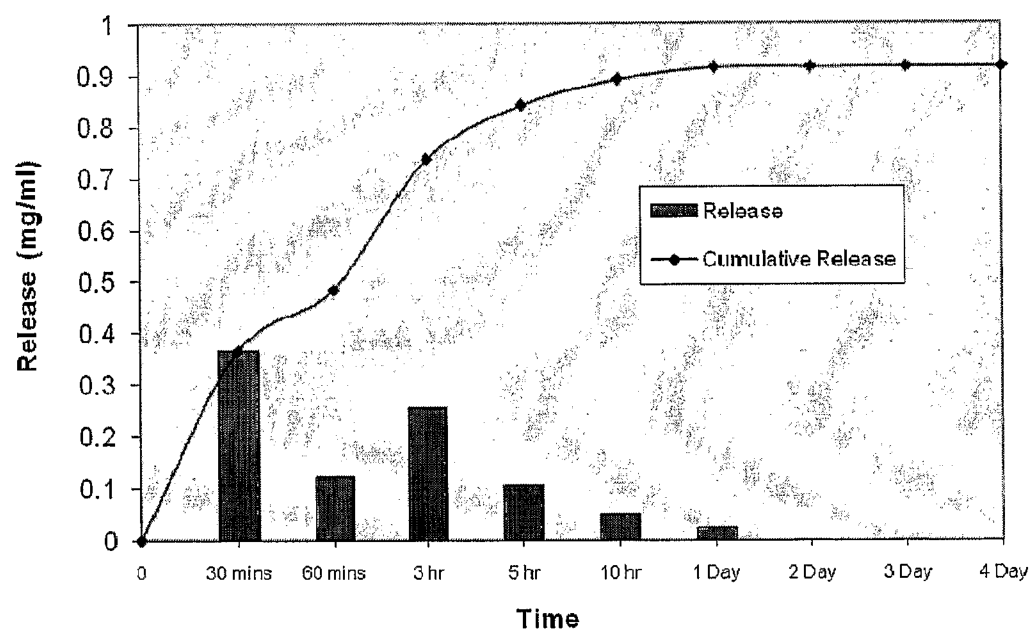
FIG. 1 shows elution profile of two different sample sets of gentamicin sulphate deposited on a beaded Ti substrate, as described in Example 1.

One embodiment provides a treatment process of depositing a therapeutically effective agent into the pores of a metal surface and subsequent removal of the agent from the outermost layers via a blasting processes, where the outermost layer is described as the surface that is visible via a line of sight process.

In one embodiment, the delivery of the active agent is performed by applying a liquid solution of the active agent onto the porous metal surface. This allows the active agent to migrate into the porous structure. In one embodiment, the coating will also contain a polymer component to cover over and slow the release of the active agent. The polymer component can be deposited simultaneously with the active agent or can be applied in a second subsequent step. Many mechanisms such as microbead encapsulation, solution spraying or dip coating are available to achieve such a polymer-drug finishes and any such process known in the art can be employed to add the polymer-active coating. In a preferred embodiment, a bioresorbable or biodegradable polymer such as PLGA, PCL or PLLA is used to control elution, as this will result in a polymer that biodegrades and is removed from the porous structure, thereby allowing the bone to grow into the open pores to deliver maximum bone fixation.

In one embodiment, the polymer component can control elution of the active agent. However, the polymer component may result in a layer on the metal implant outer surface that can impede early bone fixation to the outer surface. Such impedance can occur even when biodegradable polymers are used (see, e.g., Schnettler et al., "Glycerol-L-lactide coating polymer leads to delay in bone ingrowth in hydroxyapatite implants," *J. Controlled Release*, vol. 106, pp. 154-161 (2005).

Accordingly, one embodiment provides a further processing step to remove the polymer-drug material from the outer surface of the implant, but not from within the porous surface or porous matrix. This implant provides one or more advantages over prior art implants in which a polymer coating is deposited on a porous surface: (1) removal of the polymer from the outer surface results in the polymer/drug mixture deposited only in the pores of the implant while leaving the surface substantially free of the polymer; (2) polymer removal from the outer surface greatly reduces the amount of biodegradation needed to expose the pores, allowing initiation of bone ingrowth within the pores; (3) the reduced amount of biodegradation reduces the amount of polymer by-product released into the body; and/or (4) the exposed surface that results after polymer removal offers improved biocompatibility and enhanced osseointegration over a polymer coating.

Currently, the only drug elution surfaces for orthopedics are drug loaded cements such as Simplex P (Stryker) and Palacos G (Biomet), which offer prolonged elution over several weeks. However, this accounts only for cemented implants whereas cementless implants do not have any localized drug delivery mechanisms. Instead, the surgeon relies upon a few days of systemic antibiotic delivery to prevent infection.

In one embodiment, the removal process comprises bombarding the surface with abrasive materials, e.g., a particulate abrasive. The bombardment of metal surfaces with abrasive materials is finding an increasing number of technical applications in recent years. Techniques such as grit blasting, shot blasting, sand blasting, shot peening and micro abrasion fall under this category of surface treatment technique. In each of these techniques, generally, an abrasive material, shot or grit, is mixed with a fluid and delivered at high velocity to impinge the surface to be treated. The technique used to deliver the abrasive material can be classified as wet or dry depending on the choice of fluid medium used to deliver the abrasive to the surface, usually water and air respectively. The generic term "abrasive bombardment" is used to refer to all such techniques in this specification.

Applications of these technologies include metal cutting, cold working metallic surfaces to induce desirable strain characteristics and the pre-treatment of surfaces to induce desirable texture (surface roughness) for the purposes of enhanced adhesion of further coating materials. (See Solomon et al., Welding research, 2003. October: p. 278-287; Momber et al., Tribology International, 2002. 35: p. 271-281; Arola et al., J. Biomed. Mat. Res., 2000. 53(5): p. 536-546; and Arola and Hall, Machining science and technology, 2004. 8(2): p. 171-192). An example of the latter is to be found in the biomedical sector where titanium implants are grit blasted with alumina or silica to achieve an optimum level of surface roughness that will maximize the adhesion of plasma sprayed hydroxyapatite (HA) coatings on the surface of the implants. HA coated implants are desirable because of the biomimetic properties of the apatite layer. However, optimum bonding strength between the titanium surface and the apatite layer is not easily achieved.

It has been known that bombardment of metal surfaces can result in some of the abrasive material impregnating the surface of the metal itself. The presence of these impurities is unacceptable in the field of medical devices where governmental (FDA) approval requires strict control of the compositional makeup of devices that are to be implanted in a human body.

One study has looked at grit blasting as a means of putting a hydroxyapatite layer directly on to a titanium surface in an effort to bypass the costly plasma spray process (Ishikawa, K., et al., *Blast coating method: new method of coating titanium surface with Hydroxyapatite at room temperature*. J. Biomed. Mat. Res., 1997. 38: p. 129-134). In this study, HA of an unspecified particle size distribution was used as the abrasive. However, given that the deposited layer of apatite could be removed with a benign washing regime it seems that a strong bond with the surface of the metal was not achieved.

WO2008/033867 discloses a process in which both an abrasive and a dopant are used to treat a surface the disclosure of which is incorporated herein by reference. This has been shown to produce an effective treatment of the surface in which the dopant is intimately attached to the surface. If HA is used as the dopant, then it has been shown that an adherent HA surface finish is applied by this technique.

Accordingly, one embodiment provides a method of treating a medical implant having a porous surface, comprising:

delivering a polymer and a therapeutically active agent to the porous surface; and delivering at least one particle stream from at least one fluid jet to the implant, wherein the particle stream removes at least 90% of the polymer from the outer surface of the implant, such that the medical implant comprises the polymer and therapeutic agent impregnated within the pores of the implant.

In one embodiment, the particle stream removes at least 90%, at least 95%, or at least 99% of the polymer from the outer surface of the implant, which results in removal of at least 90%, at least 95%, or at least 99% of the polymer-drug material (polymer/therapeutic agent mixture) that was initially delivered, from the outer surface of the implant. In another embodiment, all of the polymer-therapeutic agent is removed from the outer surface, i.e., a surface that is visible via a line of sight is free of the polymer-therapeutic agent.

A medical implant having a porous surface can comprise a material that is completely porous, a material that has a solid bulk and a porous surface layer (that is of the same or a different material from the bulk, e.g., a porous calcium phosphate deposited on a metal surface), and beaded surfaces where, beads of a material (same or different from the bulk) are adhered to a bulk material.

In one embodiment, the porous surface has an average pore size ranging from 200 to 300 μm. This size has been determined to be optimal for certain orthopedic applications, as described in Bolyn, et al. The Optimum Pore Size for the Fixation of Porous Surfaced Metal Implants by the Ingrowth of Bone. CORR, 150, 1980.

In another embodiment, other researchers have achieved positive results with larger pore sizes of up to 550 microns (S. Cook et al, Optimum Pore Size for Bone Cement Fixation, Clinical Orthopaedics and Related Research. 223:296-302, October 1987).

In one embodiment, the step of delivering a polymer and a therapeutically active agent to the porous surface comprises microbead encapsulation, solution spraying or dip coating. For example, the delivering can comprise applying (e.g., via spraying or dip coating) one or more liquid solutions of the polymer and therapeutic agent to the implant, whether sequentially or simultaneously. In one embodiment, the delivering comprises applying to the implant a liquid solution comprising both the polymer and therapeutic agent. In another embodiment, the delivering comprises applying to the implant a first solution comprising the therapeutic agent, followed by applying to the implant a second solution comprising the polymer.

In one embodiment, the step of delivering at least one particle stream from at least one fluid jet is an abrasive blasting step carried out in accordance with the process described in WO2008/033867, the disclosure of which is incorporated herein by reference. In one embodiment, the abrasive blasting is performed with abrasive particles and optionally with a combination of abrasive and dopant particles blasted at the surface through at least one fluid jet. This process can offer a biocompatible outer surface that can induce bone fixation and an inner surface from which the drug is eluted. In one embodiment, the removal step is a line of sight process to remove the outer polymer treatment and retain the active agent which is located inside the porous matrix.

In one embodiment, the dopant particles used in this blasting process comprises an osteoconductive material such as calcium phosphate, HA, or a modified apatite, where the apatite is doped with Sr, Mg, Si, Ag, carbonate, F, or a bioactive glass or other such materials known to have or impart osteoconductive properties. The delivery of dopant particles in combination with abrasive particles can result in effective removal of the polymer layer while simultaneously providing a surface finish to the outer layers of the porous structure that is osteoconductive and that may enhance early stage bone fixation.

If needed, a simple abrasive blasting step may be employed first to remove the outer polymer layers and the deposition of the osteoconditive layer can be applied in a subsequent step.

The present process allows simple application of the therapeutic agent with a controlled elution profile onto a surface that is anti-microbial, porous and has the added advantage of containing an osteoconductive surface finish. Following implantation, the polymer layer within the porous structure will dissolve or otherwise degrade and release the active agent. The actual release profile can be customized by altering the polymer structure, thickness or drug loading. As a biodegradable polymer can be employed, the polymer coating can be tailored to break down at a rate that permits the bone to penetrate into the porous structure at the required rate to maximise implant fixation.

In other embodiments, the polymer can be removed from the outer surface of the implant by other methods, so long as the removal technique is based on line of sight application and the polymer material that is buried deep within the 3D structured metal is not removed. Accordingly, another embodiment provides a method of treating a medical implant having a porous surface, comprising:

delivering a polymer and a therapeutically active agent to the porous surface; and subjecting the implant to at least one technique selected from laser ablation, micromachining, and electrical discharge machining, wherein the subjecting removes at least 90% (or at least 95%, at least 99%, or 100%) of the polymer from the outer surface of the implant, such that the medical implant comprises the polymer and therapeutic agent impregnated within the pores of the implant.

Ablation techniques such as laser ablation may be used to selectively remove polymer from the outer surface. Any appropriate laser ablation device may be employed, including broad spectrum, UV or IR lasers, which can be operated in pulsed or continuous wave modes of operation as may be required to achieve the required ablation effect. Examples of this technique are outlined by Chang et al, J. Manufacturing Processes, 1999, 1(1), pg 1-17 and also by Urech et al, Applied Surface Science, 2007, 253, pg 6409-6415. Lu at al have reviewed mechanisms for micromachining biopolymers in Advanced Drug Delivery Reviews 56 (2004) 1621-1633.

In another embodiment, conventional micromachining techniques can be used to remove the polymer from the outer surface. A review of this area is provided by J L Liow (Journal of Cleaner Production 17 (2009) 662-667).

Alternatively, electrical discharge machining can be used to erode the polymer from the outer surface. Technologies such as proton beam (Rajta et al, Nuclear Instruments and Methods in Physics Research B 210 (2003) 260-265), ion beam (Springham et al, Nuclear Instruments and Methods in Physics Research B 130 (1-4) (1997) pg 155) or electron beams (Martin et al, Microelectronic Engineering 84 (2007) 1096-1099) can also remove targeted areas of polymer.

"A polymer," as defined herein refers to homopolymers, copolymers, and blends thereof. In one embodiment, the polymer is biodegradable or bioresorbable. Any biodegradable or bioresorbable polymer can be used, including homopolymers, copolymers, and blends thereof. The biodegradable polymer can be either a synthetic or naturally occurring polymer.

Examples of synthetic polymers include synthetic homopolymers such as polyglycolide (PGA), polylactide (PLA), polycaprolactone (PCL) or poly(dioxanone) (PDO).

Examples of synthetic biodegradable copolymers includes poly(I-lactide-co-glycolide) (PLGA), poly(Caprolactone/Lactide), PGA-TMC—poly(glycolide-co-trimethylene carbonate), PDO-PGA-TMC—poly(glycolide-co-trimethylene carbonate-co-dioxanone), poly(propylene-fumarate) and degradable poly(ester-urethane) materials such as Degrapol® or PolyNova®. Poly(ester amides) such as CAMEO® may also be employed. Polyanhydrides such as poly[(carboxy phenoxy propane)-(sebacic acid)] may also be used, as can poly(anhydride-co-imides), such as poly[pyromellitylimidoalanine-co-1,6-bis(p-carboxyphenoxy) hexane]. Poly (ortho esters) such as Alzamar® may be used if long term elution is required, while pol(cyano-acryalte) materials can be used to deliver rapid elution over a period of hours or days. Biodegradable polyphosphazenes include poly[(amino acid ester) phosphazene] and polyphosphoesters.

Examples of naturally occurring biodegradable polymers include polysaccharides such as starch, cellulose, chitin, chitosan, alginates, hyaluronan, chondroitin sulphate and polyhydroxyalkanoates. Protein based polymers include collagen, gelatin, fibrin (fibrinogen), silk fibroin and elastin may also be used, as can synthetic pol(amino acids) such as poly (L-glutamic acid) or poly(aspartic acid). Bacterially derived biopolymers include poly(3-hydroxybutyrate) and poly(3-hydroxybutyrate-3-hydroxyvlaerate).

Instead of depositing a polymer/therapeutic agent to the implant, another embodiment involves delivery of a phospholipid and therapeutic agent to the implant. A method of treating a medical implant having a porous surface, comprising:

delivering a phospholipid and a therapeutically active agent to the porous surface; and delivering at least one particle stream from at least one fluid jet to the implant, wherein the particle stream removes at least 90% of the phospholipid from the outer surface of the implant, wherein the medical implant comprises the phospholipid and therapeutic agent impregnated within the pores of the implant.

In one embodiment, the at least one phospholipid is selected from phosphatidylcholine, phosphtidylserine, and phosphorylcholine.

"A therapeutic agent," refers to one or more therapeutic agents. Exemplary classes of therapeutic agents that can be employed in this system include anti-cancer drugs, anti-inflammatory drugs, immunosuppressants, an antibiotic, heparin, a functional protein, a regulatory protein, structural proteins, oligo-peptides, antigenic peptides, nucleic acids, immunogens, and combinations thereof.

In one embodiment, the therapeutic agent is chosen from antithrombotics, anticoagulants, antiplatelet agents, thrombolytics, antiproliferatives, anti-inflammatories, antimitotic, antimicrobial, agents that inhibit restenosis, smooth muscle cell inhibitors, antibiotics, fibrinolytic, immunosuppressive, and anti-antigenic agents.

Exemplary anticancer drugs include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus,* calmette-guerin (BCG), Baker's Antifol (soluble), beta-2'-deoxythioguanosine, bisantrene HCl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

Exemplary therapeutic agents include immunogens such as a viral antigen, a bacterial antigen, a fungal antigen, a parasitic antigen, tumor antigens, a peptide fragment of a tumor antigen, meta static specific antigens, a passive or active vaccine, a synthetic vaccine or a subunit vaccine.

The therapeutic agent may be a protein such as an enzyme, antigen, growth factor, hormone, cytokine or cell surface protein.

The therapeutic agent may be a pharmaceutical compound such as an anti-neoplastic agent, an anti-bacterial agent, an anti parasitic agent, an anti-fungal agent, an analgesic agent, an anti-inflammatory agent, a chemotherapeutic agent, an antibiotic or combinations thereof.

The therapeutic agent could also be growth factors, hormones, immunogens, proteins or pharmaceutical compounds that are part of a drug delivery system such as those immobilized on zeolite or polymeric matrices, biocompatible glass or natural porous apitic templates such as coralline HA, demineralised bone, deproteinated bone, allograft bone, collagen or chitin.

In one embodiment, the therapeutic agent is an anti-inflammatory drugs selected from non-steroidal anti-inflammatory drugs, COX-2 inhibitors, glucocorticoids, and mixtures thereof. Exemplary non-steroidal anti-inflammatory drugs include aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone, acetaminophen, and mixtures thereof. Exemplary COX-2 inhibitors include nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof. Exemplary glucocorticoids are include hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof Other exemplary therapeutic agents include cell cycle inhibitors in general, apoptosis-inducing agents, antiproliferative/antimitotic agents including natural products such as vinca alkaloids (e.g., vinblastine, vincristine, and vinorelbine), paclitaxel, colchicine, epidipodophyllotoxins (e.g., etoposide, teniposide), enzymes (e.g., L-asparaginase, which systemically metabolizes L-asparagine and deprives cells that do not have the capacity to synthesize their own asparagine); antiplatelet agents such as G(GP) $II_b/III_a$ inhibitors, GP-IIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes-dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (e.g., estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fluorocortisone, prednisone, prednisolone, 6α-methylprednisolone, triamcinolone, betamethasone, and dexamethasone), non-steroidal agents (salicylic acid derivatives e.g., aspirin; para-aminophenol derivatives e.g., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); antigenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retinoid; cyclin/CDK inhibitors; HMG co-enzyme reductase inhibitors (statins); and protease inhibitors (matrix protease inhibitors).

In one embodiment, the therapeutic agent is an antibiotic chosen from tobramycin, vancomycin, gentamicin, ampicillin, penicillin, cephalosporin C, cephalexin, cefaclor, cefamandole and ciprofloxacin, dactinomycin, actinomycin D, daunorubicin, doxorubicin, idarubicin, penicillins, cephalosporins, and quinolones, anthracyclines, mitoxantrone, bleomycins, plicamycin (mithramycin), mitomycin, and mixtures thereof.

In one embodiment, the therapeutic agent is a protein chosen from albumin, casein, gelatin, lysosime, fibronectin, fibrin, chitosan, polylysine, polyalanine, polycysteine, Bone Morphogenetic Protein (BMP), Epidermal Growth Factor (EGF), Fibroblast Growth Factor (bFGF), Nerve Growth Factor (NGF), Bone Derived Growth Factor (BDGF), Transforming Growth Factor-.beta.1 (TGF-.beta.1), Transforming Growth Factor-.beta. (TGF-.beta.), the tri-peptide arginine-glycine-aspartic acid (RGD), vitamin D3, dexamethasone, and human Growth Hormone (hGH), epidermal growth factors, transforming growth factor $\alpha$, transforming growth factor $\beta$, vaccinia growth factors, fibroblast growth factors, insulin-like growth factors, platelet derived growth factors, cartilage derived growth factors, interlukin-2, nerve cell growth factors, hemopoietic cell growth factors, lymphocyte growth factors, bone morphogenic proteins, osteogenic factors, chondrogenic factors, or and mixtures thereof.

In one embodiment, the therapeutic agent is a heparin selected from recombinant heparin, heparin derivatives, and heparin analogues or combinations thereof.

In one embodiment, the therapeutic agent is an oligo-peptide, such as a bactericidal oligo-peptide.

In one embodiment, the therapeutic agent is an osteoconductive or osteointegrative agent.

In one embodiment, the therapeutic agent is an immunosuppressant, such as cyclosporine, rapamycin and tacrolimus (FK-506), ZoMaxx, everolimus, etoposide, mitoxantrone, azathioprine, basiliximab, daclizumab, leflunomide, lymphocyte immune globulin, methotrexate, muromonab-CD3, mycophenolate, and thalidomide.

In one embodiment, the therapeutic agent is selected from:

- Antiobiotics, including: aminoglyucosides such as gentamicin, amikacin, tobramycin; cefalosporins such as cefazolin and cefoperazone; glycopeptides such as vancomycin; macrolides such as erythromycin; nitromadazoles such as metronidazole; penicillins such as ampicillin; polypeptides such as colistin; quinolones such as ciprofloxacin or ofloxacin; rifamycins such as rifampin; tetracyclines such as doxycycline, minocycline and tetracycline; silver or any other antibiotic;
- Bisphosphonates, including: Zoledronate, Pamidronate or Ibandronate;
- Antiinflammatory agents such as NSAIDs. Aspirin, diclofenac, ibuprofen;
- Cathepsin K inhibitors such as cystatins;
- Biological factors;
- Recombinant and naturally extracted Bone morphogenetic proteins, such as BMP-2, OP-1;
- Antimicrobial peptides such as Dermcidin;
- Nucleic acids;
- Growth factors such as transforming growth factor (TGF) $\alpha$, TGF-$\beta$, basic fibroblast growth factor, Fibroblast Growth Factor-2, platelet derived growth factor; and
- Osteotropic agents such as osteoclast differentiation factor, parathyroid hormone, 1,25-dihroxyvitamin D3, and IL-11.

In one embodiment, the polymer material is a polymer such as PLLA-poly-glycolic acid (PGA) copolymer (PLGA), polycaprolactone, poly-(hydroxybutyrate/hydroxyvalerate) copolymer, or a biopolymer selected from polysaccharides, gelatin, collagen, alginate, hyaluronic acid, alginic acid, carrageenan, chondroitin, pectin, chitosan, and derivatives, blends and copolymers thereof.

In one embodiment, the medical implant has a porous metal surface comprising a metal chosen from pure metals, metal alloys, intermetals comprising single or multiple phases, intermetals comprising amorphous phases, intermetals comprising single crystal phases, and intermetals comprising polycrystalline phases, and combinations and alloys thereof. Exemplary metals include titanium, titanium alloys (e.g., NiTi or nitinol), ferrous alloys, stainless steel and stainless steel alloys, carbon steel, carbon steel alloys, aluminum, aluminum alloys, nickel, nickel alloys, nickel titanium alloys, tantalum, tantalum alloys, niobium, niobium alloys, chromium, chromium alloys, cobalt, cobalt alloys, precious metals, and precious metal alloys. In one embodiment, the metal is titanium.

In one embodiment the abrasive material is alumina (10 Mesh). In another embodiment, the abrasive material is a silica bead having a Mohs hardness ranging from 0.1 to 10, e.g., ranging from 2 to 10, or from 5 to 10. In a preferred embodiment, the abrasive is a sintered apatite such as MCD (Himed, New York) or a bioglass.

In one embodiment, the particle stream comprises particles having sizes ranging from 10 μm to 1000 microns. In another embodiment, the particle stream comprises particles having sizes ranging from 500-750 μm. The latter size range can minimize particles blocking the open pores of the porous surface.

In one embodiment, the particle stream is delivered to the metal substrate using a standard grit blasting machine operating in the pressure range of 0.5 Bar to 20 Bar, such as a pressure range of 2 to 10 bar, or a pressure range of 4 Bar to 6 Bar. The distance between the nozzle and the surface can be in the range of 0.1 mm to 100 mm, such as a range of 0.1 mm to 50 mm, or a range of 0.1 mm to 20 mm. The angle of the nozzle to the surface can range from 10 degrees to 90 degrees, such as a range of 30 degrees to 90 degrees, or a range of 70 to 90 degrees.

One of ordinary skill in the art can appreciate the influence of machine parameters including jet velocity, operating pressure, venturi configuration, angle of incidence and surface to nozzle distances on the extent of impregnation of the biocompatible material and therapeutic agent.

One of ordinary skill in the art can appreciate the effect of the size, shape, density and hardness of the abrasive material used.

One of ordinary skill in the art can appreciate the effect of the fluid stream itself, the blasting equipment using a gas medium (typically air) the effects of using inert gases as a carrier fluid e.g. N2 or noble gases such as Ar and He on the extent of removal of the biocompatible material and therapeutic agent.

In the case of wet blasting equipment using a liquid as a carrier fluid (normally water), one of ordinary skill in the art can appreciate the effect of acidity and basicity on the extent of impregnation of the biocompatible material and therapeutic agent.

As disclosed herein, the disclosed methods can be useful for modifying the surfaces of medical devices. In the context of medical device applications, the particle stream can further comprise materials to enhance lubricity or render a substrate radio-opaque, of enhance wear characteristics or enhance adhesion of an ad-layer, etc.

In one embodiment, therapeutic agents can evoke a response from the host tissue in vivo, enhancing the functionality of the device or the surgery, or delivering a benefit as a secondary function to the device.

The process can be used to modify, augment or treat surfaces such as to change surface characteristics/properties including one or more of:

- morphology/topography/form/texture/roughness/microstructure
- surface area
- surface porosity
- structure—order/disorder of molecular assemblies, inclusions, vacancies, and organisation
- crystallinity, size, distribution and orientation of crystals
- chemistry,
- chemical composition,
  - elemental composition
  - chemical state of elements
  - molecular composition
  - functional groups
  - molecular adlayers
  - adventitious contaminants and impurities
- oxide layer porosity, thickness and composition,
- biochemistry
- biological performance
- surface energy—lipophilic/lipophobic properties
- wetabillity—hydrophilic and hydrophobic properties,
- adsorption—physisorption and chemisorption
- electric properties—surface potentials and surface charges, dielectric constant
- magnetic properties
- optical properties—optical reflection/absorption
- surface mechanical properties—Elastic/plastic nature of surface layers, tensile/compressive forces in the surface
- surface dynamic properties—mobility of atoms and molecules The effect on the surface is such as to modify the chemistry and topography of the surface material resulting in an infinite range of manifestations. The desired outcome resulting from the treatment is influenced by:

- the substrate material and its surface characteristics
- the treatment process parameters and the environmental conditions
- the abrasive(s) and its mechanical and chemical properties, size, hardness, morphology etc
- the biocompatible material(s), therapeutic agents, and their chemical and mechanical properties.

In one embodiment, the methods described herein can provide one or more of the following feature

- a room temperature process
  - no degradation of the biocompatible material(s) or therapeutic agents due to temperature or process
  - ability to convey temperature sensitive agents to the surface intact.
- one step process that is manufacturing friendly
- no laminate layer results—cannot be chipped or peeled off
- adaptable to allowing implants to be custom treated for specific applications

EXAMPLES

Example 1

This example describes the modification of an implantable titanium hip stem containing a porous beaded surface. A Summit hip stem (DePuy) with a Porocoat finish was used as the substrate. The active chosen for study was gentamicin sulphate (GS).

The stem was first coated GS by dissolving 0.6 g of GS in 10 ml of water and applying the solution to the surface drop wise. In total, 0.1575 g of GS was added to the surface. Once dry, a polymer overcoat was applied by adding a solution of PLGA (3.5 g of PLGA in 10 ml of dichloromethane) dropwise and allowing to dry The coated hip stem was then abrasively blasted as per WO2008/033867 to remove the outer layer of polymer. Blasting was carried out in a Comco Standard Lathe operating at a pressure of 100 psi. MCD abrasive grit (Supplied by Himed, New York) was used as the abrasive and HA (SAI, France) was used as the dopant. Each powder was fed in a separate stream at the surface at a pressure of 100 psi and with an offset distance of 15-25 mm. The blast device was moved over the surface at a speed of approximately 100 mm/sec.

Inspection of the surface after blasting clearly revealed that the polymer layer had been removed from the outer surface. Elution of the drug from the surface was evaluated by immersing the entire hip stem in 300 ml of phosphate saline buffer and measuring drug concentration in solution using an Abbott TDx/FLX system.

FIG. 1 is an elution profile of GS from a porous beaded hip stem treated with a two step coat and abrasive blast process As shown in using an Abbott TDx/FLX system.

FIG. 1, there is evidence of gentamicin release over the 4 days of the investigation; with the bulk of the drug being released within the first day which is a similar timeframe to the current clinical schedule for use of intravenous antibiotics during implant.

Example 2

A 25 mm diameter coupon with a sintered titanium beaded surface was used as the test substrate. The titanium surface had an average pore size ranging from 200-300 microns. Vancomycin was dissolved in water to produce a solution of 0.5 g/25 ml. 0.5 ml of this solution was then applied in droplet form to the surface of each sample coupon and allowed to dry in an oven at 40° C. This technique was repeated three times to give a total loading of 1.5 ml of the vancomycin solution per coupon.

PLGA polymer (2.5 g) was dissolved in 50 mL of dichloromethane solvent. The polymer solution was added to the surface of the drug loaded coupons in a dropwise fashion similar to that employed to deploy the drug. Again, three applications of 0.5 ml were applied to produce a single layer of polymer with sufficient time being allowed between each application to allow the solvent to evaporate.

To investigate the effect of polymer coating thickness, a second set of three PLGA solutions were applied to form a batch of samples with 6 applications of polymer in total. This produced a sample with twice the coating thickness and is therefore herein referred to as having two layers of polymer.

All samples were then treated with an abrasive blasting process as described in WO2008/033867. The equipment platform was a Comco Standard Lathe. Two nozzles were employed to deliver an abrasive and a dopant respectively. The abrasive chosen was MCD 106 microns (Himed, NY, USA) and the dopant was hydroxyapatite (25/60 microns, SAI, France). The abrasive was delivered at a pressure of 75 psi and the dopant was delivered at 90 psi. The substrate was moved at a speed of 13 mm/sec relative to the nozzles. Once completed, visual examination at 10× magnification suggested that the polymer layer had been removed from the outer surface and a thin layer of hydroxyapatite had been deposited on the outer surface.

Figure 2:
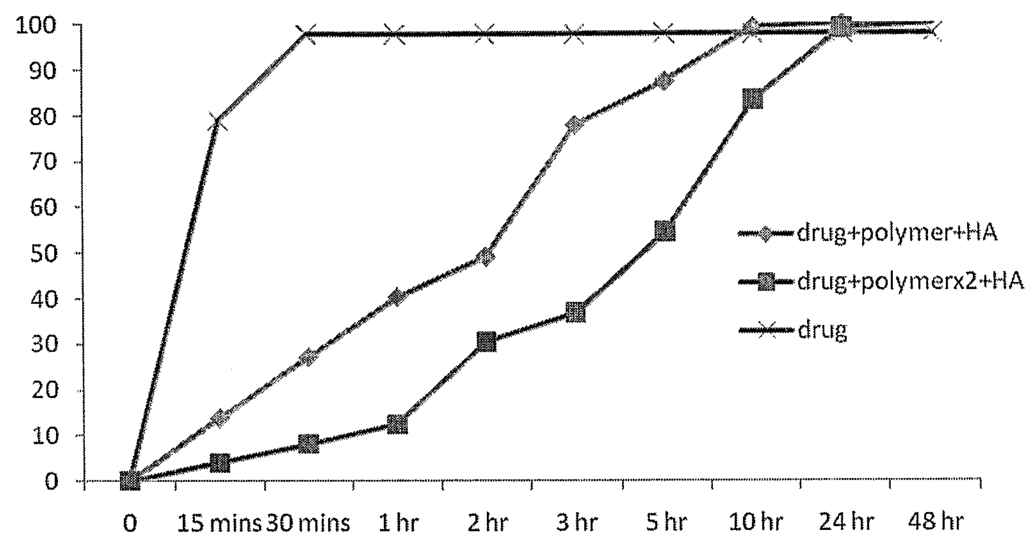
FIG. 2 shows an elution profile (% drug versus time) of vancomycin from a beaded Ti surface, as described in Example 2.

Drug elution studies were carried out in PBS buffer solution and drug concentrations were determined using an Agilent 8453 UV/VIS spectrophotometer system. The elution profile of samples with zero, one and two layers of polymer were determined over 48 hours and the % vancomycin elution was determined. Results are shown in FIG. 2, which shows an elution profile (% drug versus time) of vancomycin from a beaded Ti surface. In the absence of any polymer coating, the drug had effectively eluted form the surface within 30 minutes and no further elution was detected. Samples prepared with a single layer of polymer (3 applications of PLGA) showed prolonged elution over several hours and complete elution took up to 10 hours. Samples prepared with twice the thickness of polymer (6 applications of PLGA) showed elution out to 24 hours.

This data clearly shows that the elution profile (% drug eluted versus time) can be altered through modifications of the polymer layer and the elution profile can be altered by varying the thickness of the polymer layer It can be concluded from these results that the process was effective in removing the polymer layer from the outer surface of the implant. This creates a surface structure which contains a reservoir of antibiotic (or other therapeutically active agent) which is loaded within a biodegradable polymer deep within the three dimensionally structured surface. The substrate also has an outer surface that is polymer free and which contains an osteoconductive material (in this case hydroxyapatite) and which also retains the open porous structure which is known to optimize osseointegration.

This combination of effects offers significant advantages over the existing solutions for cementless implants, which are known to suffer from significant levels of microbial infection. The surface described herein offers the ability to provide prolonged elution of a therapeutic agent over a controlled time period, while also retaining the open, porous structure of modern hard tissue implants. Furthermore, the outermost layer of the implant provides a polymer free surface onto which osteoblast cells can adhere and proliferate, thereby inducing rapid early stage bone fixation. Furthermore, as the biocompatible polymer is degraded and removed from the bulk of the porous structure, this facilitates in-growth of the bone tissues into the three dimensional structure, providing an optimized long term fixation of the implant into the bone.

The result of this is an implant with excellent osteoconductivity, long term stability and the ability to reduce infection at the implant site, which is a clear advantage over current cementless hard tissue implants that lack any form of infection preventing capabilities.

The invention claimed is:

1. A method of treating a medical implant having a porous surface, comprising:

delivering a polymer and a therapeutically active agent to the porous surface; and delivering at least one particle stream from at least one fluid jet to the implant, wherein the particle stream removes at least 90% of the polymer from the outer surface of the implant, such that the medical implant comprises the polymer and therapeutic agent impregnated within the pores of the implant.

2. The method of claim 1, wherein the delivering at least one particle stream removes at least 95% of the polymer from the outer surface of the implant.

3. The method of claim 1, wherein the delivering at least one particle stream removes at least 99% of the polymer from the outer surface of the implant.

4. The method of claim 1, wherein the delivering at least one particle stream removes all of the polymer from the outer surface of the implant.

5. The method of claim 1, wherein the delivering at least one particle stream is also used to impart an osteoconductive material to the outer surface of the implant.

6. The method of claim 1, wherein the delivering a polymer and a therapeutically active agent comprises applying one or more liquid solutions of the polymer and therapeutic agent to the implant.

7. The method of claim 6, wherein the delivering comprises applying to the implant a liquid solution comprising both the polymer and therapeutic agent.

8. The method of claim 6, wherein the delivering comprises applying to the implant a first solution comprising the therapeutic agent, followed by applying to the implant a second solution comprising the polymer.

9. The method of claim 6, wherein the applying comprises spray-coating or dip-coating.

10. The method of claim 1, wherein the delivering at least one particle stream comprises delivering a first set of particles comprising a dopant and a second set of particles comprising an abrasive from at least one fluid jet to the porous surface to impregnate the outer surface of the implant with the dopant.

11. The method of claim 10, wherein the dopant comprises an osteoconductive or osteointegrative agent.

12. The method of claim 10, wherein the dopant comprises a calcium phosphate or modified calcium phosphate.

13. The method of claim 10, wherein the dopant is selected from a hydroxyapatite, a tricalcium phosphate, and a modified apatite.

14. The method of claim 13, wherein the modified apatite contains one or more of Sr, Zn, Mg, F, carbonate, Ag, Si, and combinations thereof.

15. The method of claim 10, wherein the dopant is bioglass.

16. The method of claim 1, wherein the medical implant has a porous metal surface.

17. The method of claim 16, wherein the porous metal surface comprises a metal selected from titanium, titanium alloys (e.g., NiTi or nitinol), ferrous alloys, stainless steel and stainless steel alloys, carbon steel, carbon steel alloys, aluminum, aluminum alloys, nickel, nickel alloys, nickel titanium alloys, tantalum, tantalum alloys, niobium, niobium alloys, chromium, chromium alloys, cobalt, cobalt alloys, precious metals, and precious metal alloys.

18. The method of claim 16, wherein the porous surface has an average pore size ranging from 200 to 300 JJm.

* * * * *